(12) United States Patent
Kim et al.

(10) Patent No.: US 6,797,631 B2
(45) Date of Patent: Sep. 28, 2004

(54) HIGH SENSITIVE MICRO-CANTILEVER SENSOR AND FABRICATING METHOD THEREOF

(75) Inventors: Tae-Song Kim, Seoul (KR); Hyung-Joon Kim, Seoul (KR); Yong-Bum Kim, Seoul (KR)

(73) Assignee: Korea Institute of Science and Technology, Seoul (KR)

( * ) Notice: Subject to any disclaimer, the term of this patent is extended or adjusted under 35 U.S.C. 154(b) by 169 days.

(21) Appl. No.: 10/209,866

(22) Filed: Aug. 2, 2002

(65) Prior Publication Data

US 2003/0032293 A1 Feb. 13, 2003

(30) Foreign Application Priority Data

Aug. 7, 2001 (KR) ......................................... 2001-47463
Aug. 7, 2001 (KR) ......................................... 2001-47464

(51) Int. Cl.[7] ............................................. H01L 21/301
(52) U.S. Cl. ....................................... 438/700; 438/719
(58) Field of Search ................................. 438/700, 704, 438/719, 720; 257/254, 417

(56) References Cited

U.S. PATENT DOCUMENTS

| 5,537,863 A | * | 7/1996 | Fujiu et al. ................... 73/105 |
| 5,914,507 A | * | 6/1999 | Polla et al. ................... 257/254 |
| 6,010,919 A | * | 1/2000 | Matsuhiro et al. ........... 438/52 |
| 6,126,311 A | * | 10/2000 | Schuh ........................ 374/21 |
| 6,420,706 B1 | * | 7/2002 | Lurie et al. ............... 250/338.1 |

* cited by examiner

Primary Examiner—Kin-Chan Chen
(74) Attorney, Agent, or Firm—McDermott Will & Emery LLP

(57) ABSTRACT

A high-sensitive micro cantilever sensor and a method for fabricating the same which is able to reduce size of a system greatly using a functional thin film has a structure in which an upper substrate comprising one or two piezoelectric cells including a cantilever, a piezoelectric layer formed on lower or upper surface of the cantilever, and electrodes formed on upper and lower surfaces of the piezoelectric layer is attached to a lower substrate including a cavity of an even depth by contacting the lower surface of the piezoelectric cell on the upper substrate with the cavity surface of the lower substrate.

7 Claims, 7 Drawing Sheets

HIGH SENSITIVE MICRO-CANTILEVER SENSOR AND FABRICATING METHOD THEREOF

BACKGROUND OF THE INVENTION

1. Field of the Invention

The present invention relates to a sensor using a functional thin film, and particularly, to a high sensitive micro-cantilever sensor and fabricating method thereof for reducing a size of a system, and for realizing a sensor of high sensitivity.

2. Description of the Background Art

Recently, miniaturized sensors based on a micro electron machine system (MEMS) process which integrates electric and machinery components to be micro size have rapid response property, and high sensitivity, and are suitable for mass production.

MEMS structure applies semiconductor fine processing technology, in which processes such as deposition and etching are repeated, to make micro products mass produced, and is operated by using electrostatic force, that is, pulling force between electric charges, magnetic force, and driving force by heat expansion difference. In addition, the MEMS has micro size and the power consumption can be reduced greatly, and therefore, the importance of the MEMS structure is emphasized with a system on chip (SOC) technology.

Recently, researches for developing sensors based on a cantilever fabricated by the MEMS process for detecting physical phenomena or chemical reactions are being processed actively.

Most of the conventional cantilever sensors measure static deflection caused by the heat or mass changing, or the change of resonant frequency using light source such as laser. However, it is difficult to reduce the size of the conventional sensor using the light source since the light source should be constructed.

FIG. 1 is a view showing the conventional cantilever sensor using the light source.

As shown therein, according to the conventional cantilever sensor, when a driving portion 11 detects the static deflection caused by the heat of the detecting material 12 or by the change of mass, or the change of the resonant frequency, sensing signals detected by the driving portion 11 are focused and collected into a sensing position diode 14.

In the conventional sensor, the light source 13 such as laser for changing the signal generated in the driving portion into the light signal, or the sensing position diode 14 for collecting the lights should be included, and therefore, there is a limit to reduce the size of the sensing system.

SUMMARY OF THE INVENTION

Therefore, an object of the present invention is to provide a high sensitive micro cantilever sensor and a method for fabricating thereof by which a size of a system can be greatly reduced by sensing a signal electrically to make the system suitable for mass producing, and a rapid sensing responding speed by performing driving and sensing simultaneously.

Also, it can be applied as a high sensitive humidity sensor, a mercury detecting sensor, a high-sensitive gas sensor, and a bio sensor detecting live material of few pico gram (pg)~few microgram (µg).

Also, it has a large displacement and driving power by using a piezoelectric cell of bimorph form, and therefore, it can be applied for various devices using above properties such as light switch.

The foregoing and other objects, features, aspects and advantages of the present invention will become more apparent from the following detailed description of the present invention when taken in conjunction with the accompanying drawings.

BRIEF DESCRIPTION OF THE DRAWINGS

The accompanying drawings, which are included to provide a further understanding of the invention and are incorporated in and constitute a part of this specification, illustrate embodiments of the invention and together with the description serve to explain the principles of the invention.

In the drawings.

DETAILED DESCRIPTION OF THE PREFERRED EMBODIMENTS

Reference will now be made in detail to the preferred embodiments of the present invention, examples of which are illustrated in the accompanying drawings.

A cantilever sensor according to the present invention detects a sensing signal instead of a light signal by forming a piezoelectric layer using material of high piezoelectricity such as PZT or ZnO and by measuring a resonant frequency generated from the piezoelectric layer after applying driving electric field to the piezoelectric layer.

Also, an even sensing can be made by forming even membrane, and the sensing property can be improved by forming a probe on a surface on opposite side of the surface on which the driving layer is formed in fabricating the cantilever sensor.

The high sensitive micro cantilever sensor according to the present invention includes a cantilever, an upper substrate formed by one or two piezoelectric cells including a piezoelectric layer and an electrode formed on upper and lower surfaces of the piezoelectric layer, and a lower substrate on which a cavity having even depth is formed. In addition, the lower surface of the piezoelectric cell on the upper substrate and the surface of the lower substrate on which the cavity is formed are attached together.

Also, fabricating the cantilever sensor according to the present invention is made in such method that the lower surface of the piezoelectric cell on the upper substrate which is formed on a lower part of the SOI substrate and the surface of the lower substrate on which the cavity is formed are attached, and the silicon on the upper part of the upper substrate is removed until an etch stopping layer is exposed.

Generally, the fabrication of the cantilever is made by using a thin film process, or by using thick film process.

Figure 1:
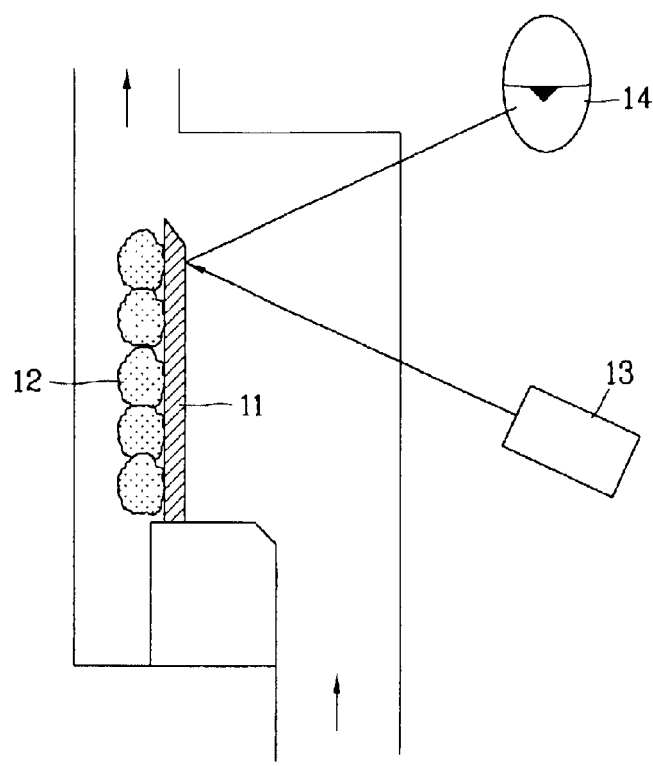
FIG. 1 is a view showing an entire structure of a conventional cantilever sensor.
Figure 2:
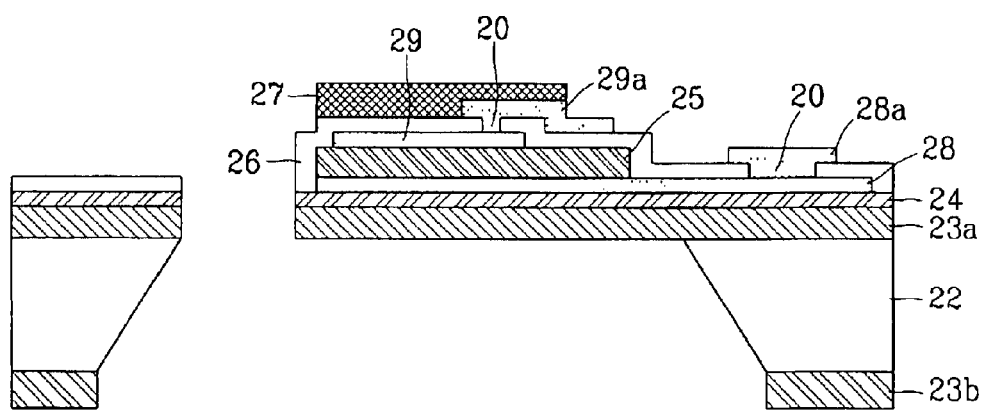
FIG. 2 is a view showing a cantilever sensor according to the present invention.

FIG. 2 is a view showing a cantilever sensor fabricated using the thin film process according to the present invention.

As shown therein, silicon nitride layers (SiNx) 23a and 23b are formed on upper and lower surfaces of the silicon substrate (100) 22, a part of the silicon nitride layer 23b formed on the lower surface of the silicon substrate (100) 22 is removed, and a part of the silicon substrate (100) 22 on the area where the silicon nitride layer 23b is removed is removed by being putted into an etchant to form a membrane of predetermined thickness.

After that, a silicon oxide layer ($SiO_2$) 24 is formed as the thickness of cantilever which will be fabricated on an upper part of the silicon nitride layer 23a, and a lower electrode 28, a driving layer 25, and an upper electrode 29 are formed on the silicon oxide layer 24 sequentially. Herein, the driving layer 25 is made of the material having high piezoelectricity such as PZT group or ZnO.

After that, a passivation layer 26 which is made of the silicon oxide film ($SiO_2$) is formed on upper entire surfaces of the upper electrode 29, the driving layer with a part exposed, and the lower electrode 28, and after that, a part of the passivation layer 26 is patterned to form a contact hole 20 which exposes some parts of the upper and lower electrodes 28 and 29.

Then, an upper electrode pad 29a and a lower electrode pad 28a which are connected electrically through the contact hole 20 are formed so that the signal is applied to the upper and lower electrodes 28 and 29 from outer side.

And a metal film 27 such as gold (Au) is deposited on the passivation layer 26 so that the biomass can be attached easily, then the fabrication of the cantilever sensor through the thin film process is completed.

The cantilever sensor uses the piezoelectric layer having high piezoelectricity as a driving layer, and the sensing is made through an electric signal applied from the outer side. Therefore, there is no need to construct a light source in the cantilever sensor, and the size of the sensor can be reduced.

However, in the cantilever sensor fabricated using the thin film process, it is difficult to form the membrane of even thickness due to the characteristics of the etching process. Also, the driving layer 25 made of the piezoelectric material is formed on the upper part of the cantilever with a large step on the surface thereof due to the physical property of the piezoelectric material. Therefore, the area of the probe which will be located on the driving layer 25 is greatly reduced, and the sensing performance of the cantilever is also reduced.

Actually, the resonant frequency of the driving layer is very sensitive to the thickness of the membrane, and therefore, uniformed sensing property can not be obtained without the membrane of even thickness.

Therefore, a cantilever sensor in which the upper substrate and the lower substrate are attached through a bulk fabrication process is fabricated in order to solve the above problem.

Hereinafter, the cantilever sensor and the method for fabricating thereof through the bulk process will be described as follows with reference to Figures.

Figure 3A:
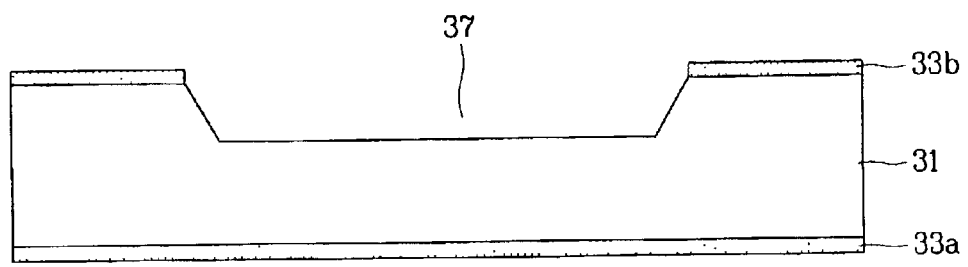
FIGS. 3a and 3b are views showing processes for fabricating a lower substrate of the cantilever sensor according to the present invention.
Figure 3B:
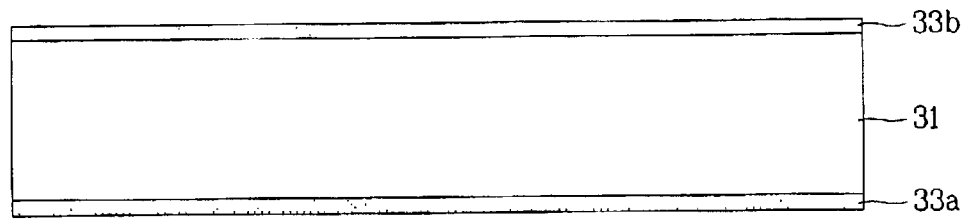

FIGS. 3a and 3b are views showing fabricating processes of the lower substrate of the cantilever sensor according to the present invention.

As shown in FIG. 3a, silicon nitride layers 33a and 33b are formed on upper and lower entire surfaces of a silicon substrate (001) 31 which can be micro machined.

And, as shown in FIG. 3b, a part of the silicon nitride layers 33b formed on the upper part of the silicon substrate, on which the silicon nitride layers 33a and 33b are formed, is removed using an etching solution, and the silicon substrate (001) 31 on the area where the silicon nitride layer 33b is removed is etched to form a cavity 37 of a predetermined thickness on that area. And a glass substrate can be used instead of the silicon substrate (001) 31.

The silicon nitride layers 33a and 33b are formed on the upper and lower surfaces of the silicon substrate (001) 31 in order to protect the silicon substrate (001) 31 from the etching solution used in forming the cavity 37 on the silicon substrate (001) 31.

The etching method for forming the cavity 37 can be wet etching method using KOH, TMAH, etc. used generally, or dry etching method such as an ion reaction etching method or an ion beam etching method.

Hereinafter, the method for fabricating an upper substrate of the cantilever sensor according to the present invention will be described as follows with reference to FIGS. 4a through 4d.

Figure 4A:
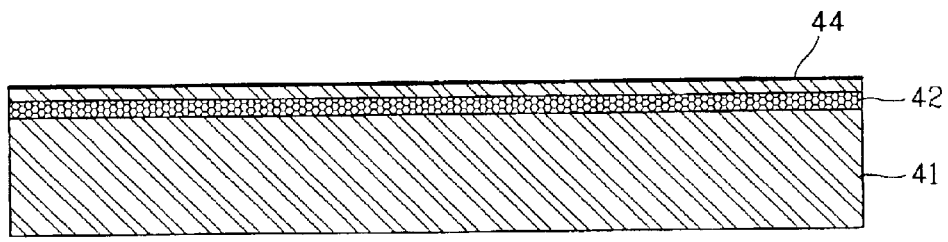
FIGS. 4a through 4d are views showing processes for fabricating an upper substrate of the cantilever sensor according to the present invention.

As shown in FIG. 4a, a silicon on insulator (SOI) substrate 41 is prepared in order to make the upper substrate of the cantilever sensor, and a heat oxide layer 44 is formed on entire upper and lower surfaces of the SOI substrate 41, on which the silicon oxide layer 42 is formed, for improving the adhesiveness with electrodes which will be formed.

Figure 4B:
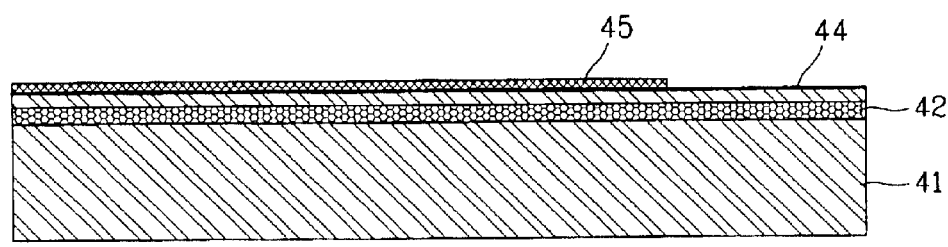

In addition, as shown in FIG. 4b, a lower electrode 45 is formed on the upper surface of the SOI substrate 41 which is covered by the heat oxide layer 44 for applying the electric field to drive.

At that time, the lower electrode 45 can be formed by using a thermal evaporation method or by using an e-beam evaporation method.

Figure 4C:
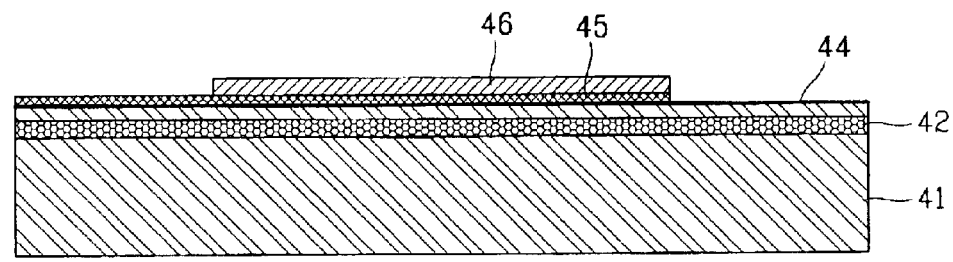

After that, as shown in FIG. 4c, a driving layer 46 having a higher piezoelectricity and a sensing layer (not shown) are formed on the lower electrode 45.

The driving layer 46 and the sensing layer are made of the piezoelectric material such as PZT group or ZnO, and the thickness of the layers can be formed variously from thin film to thick film.

The driving layer 46 and the sensing layer can be formed using a sputtering method or a chemical vapor deposition (CVD) method in case of applying the thin film to the driving layer 36 and the sensing layer. And the driving layer 46 and the sensing layer can be formed using a screen printing method or the CVD method in case of applying thick film to the driving and sensing layers. And a heat processing using a rapid thermal annealing or a conventional electric furnace is made after forming the layer in order to prevent the layer from being broken by a shock.

Figure 4D:
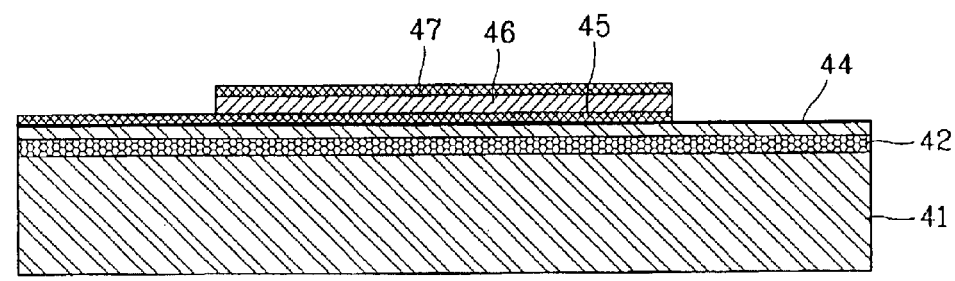

In addition, as shown in FIG. 4d, an upper electrode 47 is formed on the driving layer 46 and the sensing layer using the same method as that of the lower electrode 45. At that time, passivation layers such as the silicon oxide layer ($SiO_2$), the silicon nitride layer (SiNx), or the silicon carbonated layer (SiC) may be covered in order to prevent the device, or in order not to contact with another solutions.

The upper electrode 47 and the lower electrode 45 formed on the upper and lower parts of the driving layer 46 and the sensing layer can be formed using platinum or oxide electrode materials such as $RuO_2$ and $SrRuO_3$ which are well known as conductive oxide.

Figure 5:
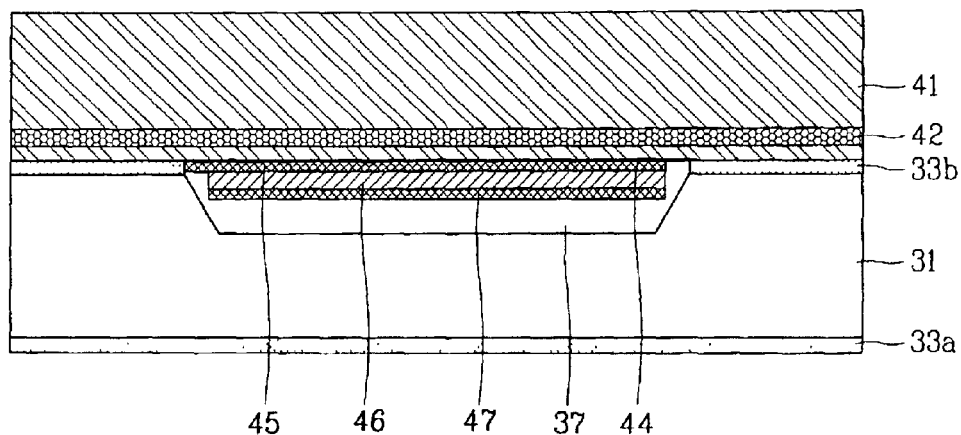
FIGS. 5 through 8 are views showing fabricating processes of the high sensitive cantilever sensor.

In addition, as shown in FIG. 5, the fabricated lower substrate and the upper substrate are attached with each other. At that time, the upper surface of the lower substrate on which the cavity 37 is formed and the upper surface of the upper substrate including the driving layer 46, and upper and lower electrodes 47 and 45 are contacted to each other.

The attachment of the upper substrate and the lower substrate can be made by using a silicon direct bonding (SDB) method, an anodic method, or by using a different kind of attaching layer such as epoxy.

Figure 6:
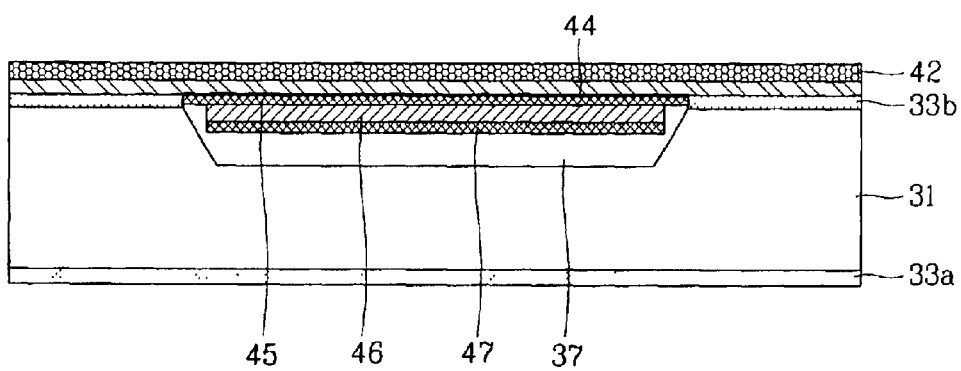

As shown in FIG. 6, the heat oxide layer 44 which is formed on the SOI substrate in order to improve the adhesiveness with the electrode material is removed, and the silicon layer (100) 41 is removed until the etch stopping layer 42 made of the silicon oxide layer is exposed to form a device on which the membrane of uniform thickness. The etch stopping layer 42 may use a low pressure silicon nitride layer or n+ silicon layer instead of the silicon oxide layer.

When the silicon layer (100) 41 of the upper substrate is etched, an electric-chemical etching method which removes the silicon in the etching solution such as KOH or TMAH, or a deep trench reaction ion etching method can be used.

Figure 7:
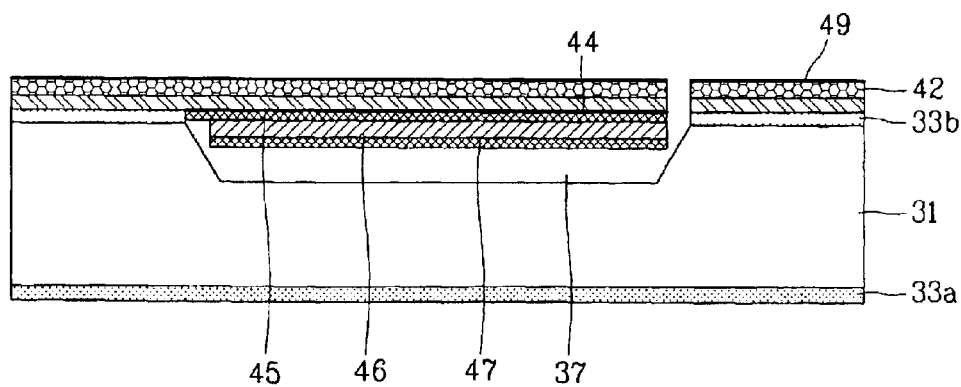

After that, as shown in FIG. 7, an Au layer 49 is formed on the entire surface of the exposed etch stopping layer 42 in order to make the biomass attach to the membrane easily, and after that, the upper substrate on which the driving layer and the electrode are formed is cut along with the end of the cavity 37.

Figure 8:
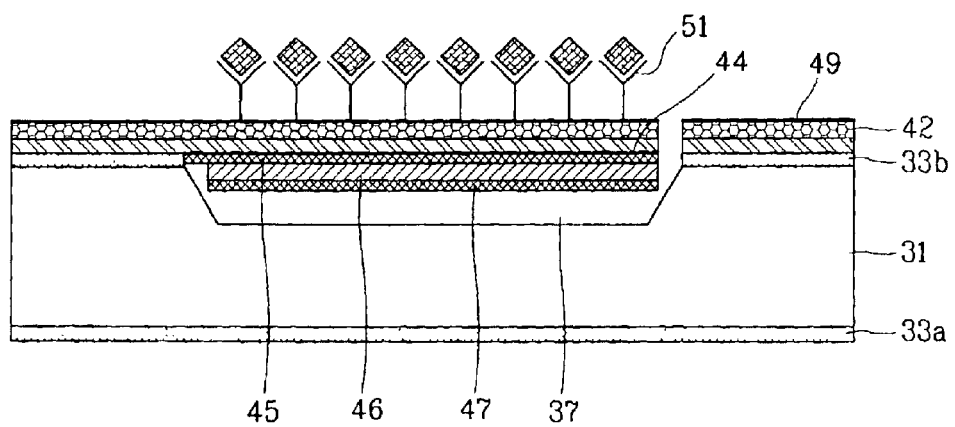

In addition, when the probe 41 is covered on the Au layer 49 area on the upper part of the driving layer 36 which is formed as corresponding to the cavity 37, the high-sensitive cantilever sensor shown in FIG. 8 can be fabricated.

Operation and sensing method of the cantilever sensor fabricated above will be described as follows.

The piezoelectric cell comprising the upper and lower electrodes and the piezoelectric layer can be divided a driving cell which is able to drive, and a sensing cell which is able to perform sensing operation. And these two are formed respectively on the lower part of the cantilever with a predetermined gap therebetween. Therefore, when the electric field corresponding to a resonant frequency of one piezoelectric cell between the above two is applied to drive the cell, the piezoelectric cell which functions sensing operation discharges the electric charge corresponding to the resonant frequency and detects the discharged electric charge. At that time, when a material is attached to the sensing layer, the resonant frequency of the driving piezoelectric cell by the fine change of mass, and the sensing cell detects the signal corresponding to the difference of electric charge caused by the difference of resonant frequency, and thereby, the sensing operation is made.

The driving method of the driving cell can use one of the above piezoelectric method, and a capacitive method selectively. The capacitive method is a method, in which an electrode is formed on the lower surface of the cantilever and the driving electric field is applied between the above electrode and the electrode formed on the cavity bottom on the lower substrate so as to vibrate as a certain frequency, and the cantilever is driven centering around the cavity and detects using the piezoelectric layer or piezo resistance layer located on the upper part of the cantilever.

Also, the sensing method of the sensing cell can be one of the piezoelectric method which detects the sensing signal from the piezoelectric layer, and a piezo resistance method which uses a strain sensor using a piezo resistance layer instead of the piezoelectric layer.

Figure 9:
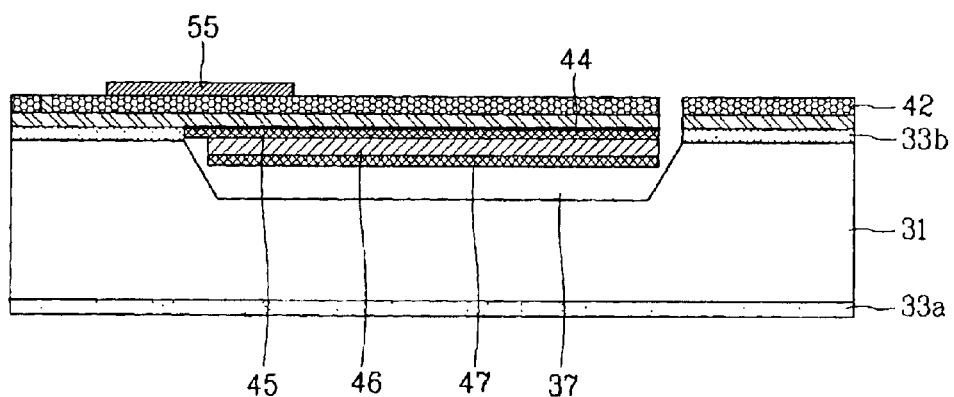
FIG. 9 is a cross-sectional view showing a cantilever sensor using a piezo resistance layer.
Figure 10:
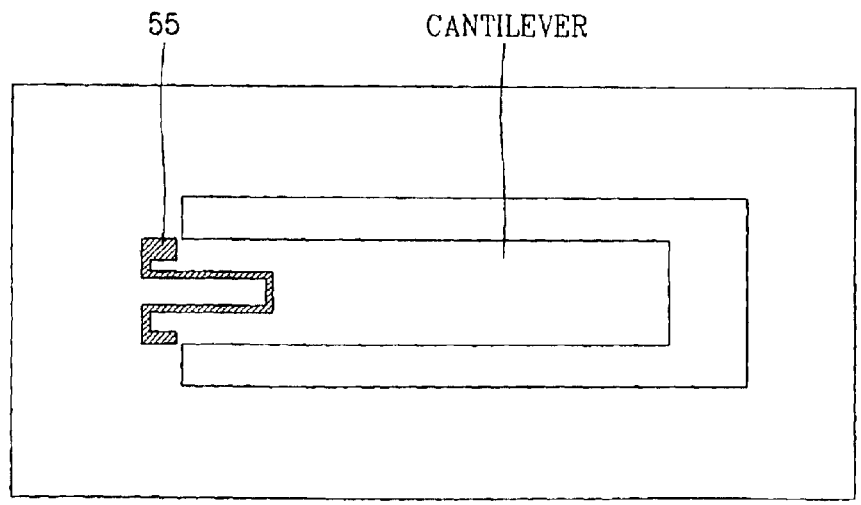
FIG. 10 is a plan view showing the cantilever sensor using the piezo resistance layer.

FIG. 9 is a cross sectional view showing a cantilever sensor using the piezo resistance layer, and FIG. 10 is a plan view showing the above cantilever.

As shown therein, the driving cell is made of the piezoelectric layer, and the sensing cell is made of the piezoresistance layer and is formed on the upper part of the cantilever.

Hereinafter, another embodiment of the present invention will be described with reference to FIGS. 11 through 15.

Figure 11:
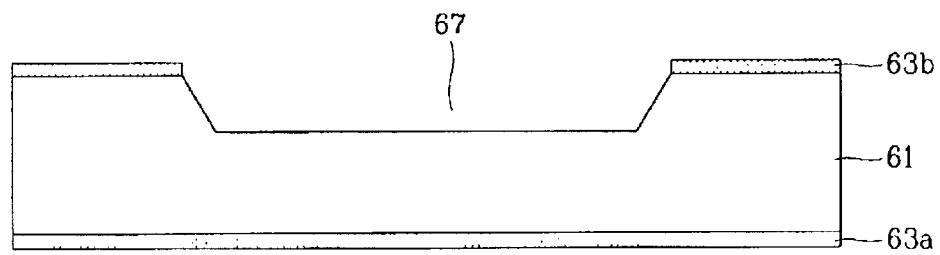
FIGS. 11 through 15 are views showing fabricating processes of the cantilever sensor according to the present invention.

As shown in FIG. 11, silicon nitride layers 63a and 63b are formed on entire upper and lower surfaces of a silicon substrate (001) 61, then, a part of the silicon nitride layer 63b formed on the upper part of the silicon substrate (001) 61 is removed using an etching solution, and the silicon substrate (001) 61 of the area where the silicon nitride layer 63b is removed is etched. In addition, a lower substrate in which a cavity 67 of a predetermined thickness is formed on the silicon substrate (001) 61 of the area where the silicon nitride layer is fabricated. At that time, the glass substrate can be used instead of the silicon substrate (001).

Figure 12:
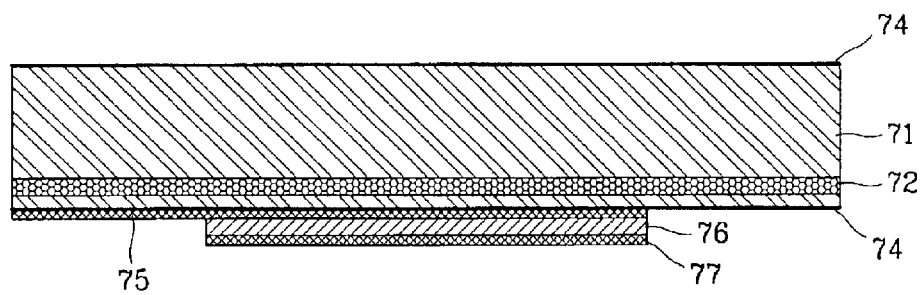

In addition, as shown in FIG. 12, an SOI substrate 71 on which a silicon oxide layer 72 is formed is prepared, and a heat oxide layer 74 is formed on entire upper and lower surfaces of the SOI substrate 71 in order to improve adhesiveness with an electrode which will be formed. After that, a lower electrode 75 is formed on the upper surface of the SOI substrate 71 so as to apply an electric field for driving, and a piezoelectric layer 76 made of a piezoelectric material such as PZT group or ZnO is formed on the lower electrode, and an upper electrode 77 is formed on the piezoelectric layer 76 to fabricate the upper substrate.

The piezoelectric layer can be applied variously from the thin film to the thick film. And platinum or conductive oxide electrode such as $RuO_2$ or $SrRuO_3$ can be used as the electrode material formed on the upper and lower parts of the piezoelectric layer 76.

In addition, a passivation layer such as silicon oxide layer ($SiO_2$), silicon nitride layer ($SiN_x$), or silicon carbide layer (SiC) may be formed in order to protect the device or to prevent contact to with other solutions.

Figure 13:
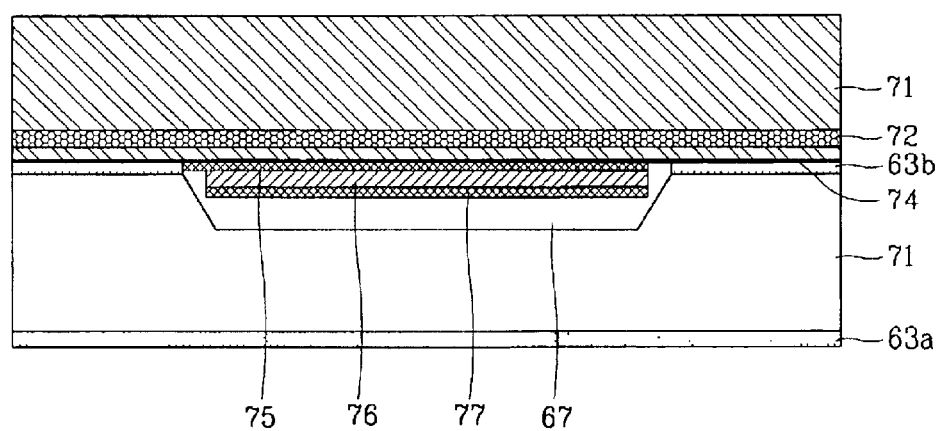

After that, as shown in FIG. 13, the upper substrate (FIG. 12) fabricated as above is attached to the lower substrate shown in FIG. 11 to form the membrane. At that time, the upper and lower substrates are attached in a manner such as SDB method, anodic method, or using an attachment layer of different kind such as epoxy. And the driving layer of the upper substrate is to be corresponded to the surface of the lower substrate on which the cavity is formed.

Figure 14:
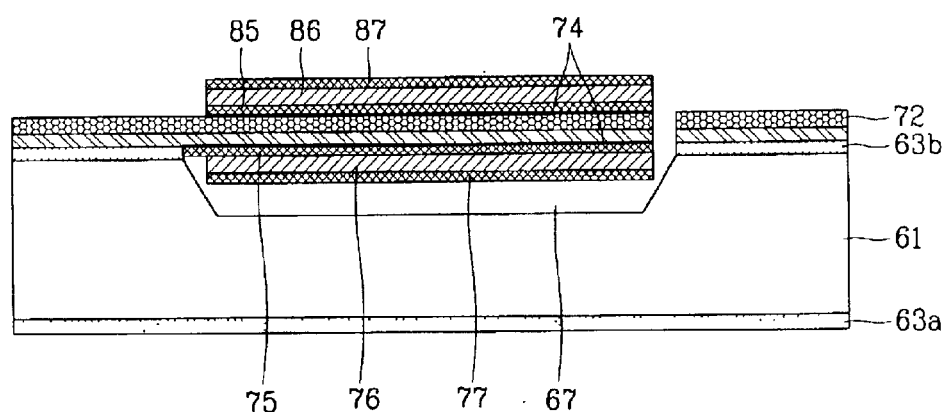

As shown in FIG. 14, the silicon substrate 71 is removed until the silicon oxide layer 72 is exposed, and the heat oxide layer 74 and the lower electrode 85 are formed on the membrane. In addition, the piezoelectric layer 86 made of piezoelectric material such as PZT group or ZnO is formed on the lower electrode 85, and the upper electrode 87 is formed on the piezoelectric layer 86. After that, the upper substrate including the piezoelectric layer and the electrodes formed on the upper and lower surfaces of the piezoelectric layer is cut along the end of the cavity 67. At that time, the heat oxide layer 74 is formed in order to improve the adhesiveness between the silicon oxide layer 72 and the lower electrode 85.

Figure 15:
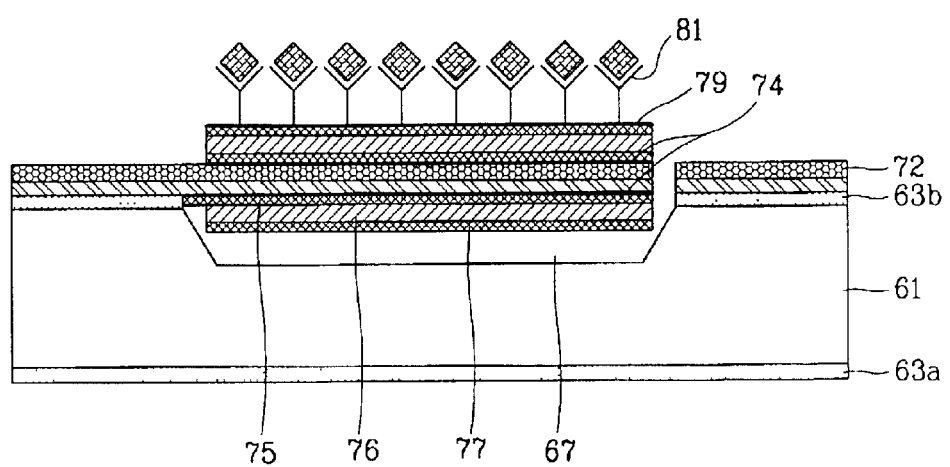

Next, as shown in FIG. 15, when the Au layer 79 is formed on the upper electrode 87 in order to make the biomass be attached easily and a bio probe 81 is formed on the Au layer 79, the high-sensitive micro bio sensor shown in FIG. 15 can be obtained. At that time, the Au layer 79 improves the adhesiveness between the bio probe 81 and the membrane.

The cantilever sensor fabricated as above can be applied to a place where the changed in weight can be detected, or can be applied as a sensor having various functions by depositing appropriate sensing layer thereon according to the material or method for detecting. If the sensing layer absorbing the humidity is applied on the cantilever, the cantilever can be used as a humidity sensor. And if the sensing layer which is able to be attached by mercury is deposited, the cantilever can be used as a mercury detecting sensor. In addition, if the sensing layer which is able to be attached by various kinds of gas is used, the cantilever can be used as a high-sensitive gas sensor. Also, the cantilever can be applied as a bio chip for detecting the biomass of a few picogram~a few microgram using a detecting material which reacts to a certain biomass as shown in FIG. 8 or FIG. 15. Also, as shown in FIG. 15, when the piezoelectric layers of bimorph shape are driven at the same time after polling them on the upper and lower parts of the cantilever, the displacement and the changing force are larger than those of an actuator of monomorph shape shown in FIG. 9, and therefore, it can be applied to a light switch or various actuators.

Operation and sensing method of the cantilever sensor fabricated in the above embodiments will be described as follows.

The piezoelectric cell comprising upper and lower electrodes and piezoelectric layer on upper or lower part of the cantilever is divided into a driving cell which drives and a sensing cell. When the electric field corresponding to the resonant frequency of one piezoelectric cell of the two is applied to drive, the driving cell discharges electric charges corresponding to the resonant frequency, and the sensing cell senses the discharged electric charges. If a material which is to be detected is attached on the sensing layer, the resonant frequency of the driving cell is changed by the fine change of mass, and the sensing cell senses the signal corresponding to the changes of electric charges which are discharged by the difference of the resonant frequency whereby the sensing operation is made.

The driving method of the driving cell may use the piezoelectric method like above, or a capacitive method which drives by applying the electric field between the electrode formed on the lower surface of the cantilever and the electrode formed on the cavity surface.

In the capacitive method, when opposite electric fields are applied to the lower electrode formed on the lower surface of the cantilever and to the electrode (not shown) formed on the cavity surface which are faced to each other centering around the cavity, the electrodes are contacted and separated to/from each other repeatedly according to the frequency of the electric fields to resonate the cantilever. And an additional electrode should be formed on the cavity surface if the capacitive driving method is used.

Also, the sensing method of the sensing cell can be both of piezoelectric method measuring the sensing signal from the piezoelectric layer, and piezo-resistance method making a strain sensor using the piezo-resistance layer instead of the piezoelectric layer.

As the present invention may be embodied in several forms without departing from the spirit or essential characteristics thereof, it should also be understood that the above-described embodiments are not limited by any of the details of the foregoing description, unless otherwise specified, but rather should be construed broadly within its spirit and scope as defined in the appended claims, and therefore all changes and modifications that fall within the metes and bounds of the claims, or equivalence of such metes and bounds are therefore intended to be embraced by the appended claims.

What is claimed is:

1. A method for fabricating a high-sensitive micro cantilever sensor comprising:

a step of preparing a silicon substrate and fabricating a lower substrate by forming a cavity of predetermined thickness on an upper surface of the silicon substrate;

a step of preparing an SOI (Silicon on Insulator) substrate and fabricating an upper substrate by forming one or two piezoelectric cells on an upper surface of the SOI substrate;

a step of attaching the lower substrate and the upper substrate so that the surface of lower substrate on which the cavity is formed and the surface of the upper substrate on which the piezoelectric cell is formed are contacted to each other;

a step of removing the silicon layer of the upper substrate until an etch stopping layer is exposed; and a step of depositing a metal layer on the etch stopping layer, and forming a sensing layer on the metal layer.

2. A method for fabricating a high-sensitive micro cantilever sensor comprising:

a step of preparing a silicon substrate and fabricating a lower substrate by forming a cavity of predetermined thickness on an upper surface of the silicon substrate;

a step of preparing an SOI (Silicon on Insulator) substrate and fabricating an upper substrate by forming one or two piezoelectric cells on an upper surface of the SOI substrate;

a step of attaching the lower substrate and the upper substrate so that the surface of lower substrate on which the cavity is formed and the surface of the upper substrate on which the piezoelectric cell is formed are contacted to each other;

a step of removing the silicon layer of the upper substrate until an etch stopping layer is exposed;

a step of forming a piezoelectric cell on the etch stopping layer; and a step of depositing a metal layer on the piezoelectric cell, and then, forming a sensing layer on the metal layer.

3. The method of claim 1 or claim 2, wherein the step of forming piezoelectric cell comprises a step of forming a lower electrode, a step of forming a piezoelectric layer on the lower electrode, and a step of forming an upper electrode on the piezoelectric layer.

4. The method of claim 1 or 2, wherein the etch stopping layer may be formed as one of silicon oxide layer, n+ silicon layer, or low pressure silicon nitride layer.

5. The method of claim 1 or claim 2, wherein a glass substrate is used instead of the silicon substrate.

6. The method of claim 1 or claim 2, wherein the metal layer is formed using Au.

7. The method of claim 1 or claim 2, wherein a heat oxide layer is additionally formed before the lower electrode is formed.

* * * * *